United States Patent [19]

Audeh

[11] 4,131,610

[45] Dec. 26, 1978

[54] IMINODIIMIDES OF 3,3',4,4'-BENZOPHENONETETRACARBOXYLIC DIANHYDRIDE AND COMPOSITIONS THEREOF

[75] Inventor: Costandi A. Audeh, Princeton, N.J.

[73] Assignee: Mobil Oil Corporation, New York, N.Y.

[21] Appl. No.: 828,379

[22] Filed: Aug. 29, 1977

[51] Int. Cl.$^2$ .................... C07D 403/06; C10M 1/32; C10M 1/36
[52] U.S. Cl. .......................... 260/326 N; 252/51.5 A
[58] Field of Search .................................. 260/326 N

[56] References Cited

PUBLICATIONS

Saidenova et al., Chem. Abs. 83, 164634 (1975).

*Primary Examiner*—Nicholas S. Rizzo
*Assistant Examiner*—Mark L. Berch
*Attorney, Agent, or Firm*—Charles A. Huggett; Raymond W. Barclay; Howard M. Flournoy

[57] ABSTRACT

Iminodiimides of 3,3',4,4'-benzophenonetetracarboxylic dianhydride are novel compounds having utility as pour depressants and as UV stabilizers when incorporated into lubricant compositions.

3 Claims, No Drawings

IMINODIIMIDES OF 3,3′,4,4′-BENZOPHENONETETRACARBOXYLIC DIANHYDRIDE AND COMPOSITIONS THEREOF

BACKGROUND OF THE INVENTION

1. Field of the Invention

This application is directed to the preparation and use of novel iminodiimides, and to compositions containing same. This application is more particularly directed to the preparation of iminodiimides of 3,3′,4,4′-benzophenonetetracarboxylic acid dianhydride and to their use as pour depressants and UV stabilizers in lubricants.

2. Description of the Prior Art

The use of amines in lubricant compositions or amino compounds is well known, e.g., phenyl-alpha-naphthyl amine as an antioxidant additive. However, an amino-derived compound which concomitantly possesses pour depressant properties and UV stabilization characteristics was, as far as is known, unknown prior to now. Additionally, the compounds (iminodiimides) in accordance herewith also as far as is known are believed to be novel.

SUMMARY OF THE INVENTION

This invention is therefore directed to the preparation of a novel class of compounds, to the compounds per se and to a method of using them as pour point depressants and/or UV stabilizers in various organic media, e.g., hydrocracked liquid hydrocarbons and distillate fuels.

A primary amine is reacted with benzophenonetetracarboxylic dianhydride (BTDA) under appropriate conditions to produce the novel compounds of this invention. The general structural formula of these compounds is as shown below.

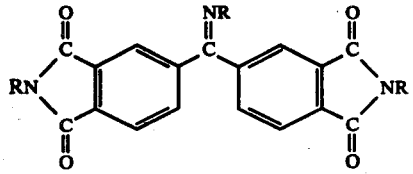

where R preferably is H or an alkyl group, branched or straight, having from 1 to about 36 carbon atoms. R may also be aryl, alkaryl or aralkyl having from 6 to about 36 carbon atoms. R preferably contains 10 to 26 carbon atoms. The reaction is generally carried out at atmospheric pressure. However, pressures of up to about 200 psig and temperatures from 200° to about 400° C. may be resorted to if so desired. Preferred reaction conditions are atmospheric pressure and 230°–250° C. Further, molar ratios of the amine to the benzophenonetetracarboxylic dianhydride are from about 3 to 3.5 moles of amine to 1 mole of BTDA. Preferred molar ratio is 3 moles of amine to 1 mole of BTDA.

Any primary amine having the following general structure can be used in preparing the novel class of iminodiimides disclosed herein:

where R is alkyl, aryl, alkaryl or aralkyl or any combination thereof having from 1 to about 36 carbon atoms. Some examples thereof are methylamine, tertiary-butyl- amine, cyclohexyl amine, benzyl amine, toluidine, aniline, nonyl aniline, dodecyl aniline, naphthyl amine.

The iminodiimides described herein are effectively used in any lubricating media in which the lubricant base is a petroleum product, such as a mineral oil or a synthetic fluid. The synthetic fluids include synthetic hydrocarbons derived from long chain alkanes or olefin polymers, ester oils obtained from polyhydric alcohols and monocarboxylic alcohols and polycarboxylic acids or mixtures thereof. The lubricant media can also comprise a grease wherein a sufficient amount of the oil is employed to balance the grease after the desired amount of the thickening agent and other additive components are included in the grease formulation.

However, as mentioned heretofore, the novel additives of this invention may be used in organic media other than lubricant compositions. For example, liquid hydrocarbons such as distillate fuel oils. Accordingly, the novel additives embodied herein are adapted for use in a composition comprising a major amount of an appropriate organic medium and a minor amount effective to impart pour depressant properties and UV stabilization characteristics thereto of an iminodiimide of 3,3′,4,4′-benzophenonetetracarboxylic dianhydride.

The amount of additive compound used in the organic media may vary from about 0.025 to about 10% or more by weight of the base material, e.g., lubricant. The compositions preferably contain from about 0.05 to about 2% by weight of the additive based on the total weight of the composition. The compositions can also contain any other additive compounds known in the art such as antioxidants, antiwear and anticorrosion inhibitors without detrimentally affecting the pour depressant and UV stabilization characteristics of the subject iminodiimide additive compounds.

DESCRIPTION OF SPECIFIC EMBODIMENTS

Example 1 describes the general method of preparing the additive compounds. Examples 2 & 3 illustrate their use as UV stabilizers and Example 4 illustrates their use as pour point depressants. The BTDA is readily obtained from commercial sources.

Example 1

0.055 moles (17.5 gms) of BTDA were mixed with 0.17 moles of $C_{16}H_{33}NH_2$ and heated until reaction was complete (about 3 hours). 0.17 moles of water (3.0 gms) were collected by entrainment distillation with toluene. The resultant product was identified as having the following structure:

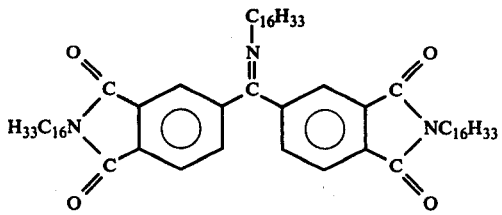

Analysis calculated: C, 78.66; H, 10.66; N, 4.23. found: C, 78.55; H, 10.60; N, 4.08. MP 60° C.

Example 2

0.1 gm of the product of Example 1 was mixed with 100 gms of a hydrocracked oil and the resultant solution tested for light stability (Windowsill Test)*. A sample of hydrocracked oil not containing an additive compound as disclosed herein was tested similarly as a "control". After one day the "control" sample, i.e., hydrocracked oil without the compound of Example 1 became hazy and precipitated brown material while the sample containing 0.1% of the compound of Example 1 did not. Further, after 8 days the sample containing the additive compound of the invention was still clear and without signs of precipitate formation.

A test wherein the material to be tested is placed on a windowsill in the sunlight and thereby exposed to U V light.

Example 3

A 1 gm sample of the product of Example 1 was tested in accordance with Example 2. After 3 months the sample (containing additive in accordance with this invention) was still clear and without signs of precipitate formation.

A fuel oil, properties shown in Table 1, was mixed with 0.5% by wt. of the product of Example 1 and tested by the falling ball type viscometer. Table 2 below contains the fuel test data.

TABLE 1
PROPERTIES OF NO. 2 FUEL OIL

| | |
|---|---|
| Sulfur total % wt. | 1.09 |
| sulfur, mercaptan % wt. | 0.0109 |
| Conradson Carbon, CCR % wt. | <.01 |
| Color, Saybolt | +8. |
| Corrosion, Copper Strip, 2 hr at 212° F | 1A |
| Density at 15° C | 0.8417 |
| Distillation, ° F, ASTM (D86) | |
| IBP | 404 |
| 10% | 499 |
| 20% | 524 |
| 50% | 556 |
| 90% | 608 |
| EP | 634 |
| Flash Point, COC, ° F | 245 |
| Flash Point, Pensky Martens, CC, ° F | 205 |
| Gum, Existent, mg/100 ml | 27.0 |
| Hydrocarbons, High Mass Spec. $C_{10}+$ | |
| Paraffins | 52.0 |
| Mononaphthenes | 15.4 |
| Polynaphthenes | 7.2 |
| Aromatics | 25.5 |

Example 4

Three samples of the fuel oil containing 0.5% of the BTDA were subjected to the below detailed pour depressant test procedure. Each was treated as indicated prior to measuring. The tests were done with a falling ball type viscometer in the following manner:

A sample of oil is placed in a graduated cylinder and thermostatically controlled to and maintained at the desired temperature. The oil is then cooled. A stainless steel ball is then dropped in the oil sample and its progress in the oil observed. As the oil sample cools down further the progress of another identical stainless steel ball is observed. The temperature at which the cooled oil does not allow such a steel ball to continue falling is then recorded. A similar sample of the reference oil is treated in an identical manner. The concentration of the additive compound of Example 1 was 0.5%.

Table 2

| Ref. Fuel | Ref. Fuel + 0.5% | Treatment |
|---|---|---|
| −8° F | −14 | Preheat at 70° C for ½ hour. Cool to R.T., then measure. |
| −9° F | −15 | " |
| −8° F | −18 | Preheat at 70° C for ½ hour. Left overnight, then heat at 90° C for ½ hour Cool to R.T., then measure. |

The data of Examples 2 & 3 and Table 2 illustrate the utility of this invention, i.e., that iminodiimides of BTDA provide excellent pour depressant and UV stabilization characteristics for liquid hydrocarbon compositions such as hydrocracked oils and distillate fuel oils.

It is understood that modifications of the exemplary embodiments disclosed herein are within the spirit and the scope of this invention.

What is claimed is:

1. A compound having the following general structure:

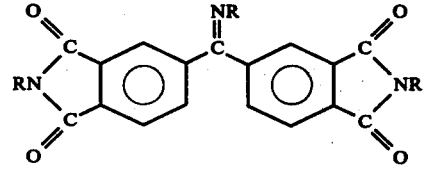

where R is H, alkyl having from 1 to 36 carbon atoms.

2. The compound of claim 1 where R is alkyl having from 10 to 26 carbon atoms.

3. The compound of claim 2 where R has 16 carbon atoms.